United States Patent [19]

Hayashi et al.

[11] 4,128,630

[45] Dec. 5, 1978

[54] COSMETICS AND PROCESS FOR PREPARATION THEREOF

[75] Inventors: Katsutake Hayashi; Tutomu Saitoh, both of Tokyo; Katsuyuki Yomogida; Hiromasa Saito, both of Yokohama, all of Japan

[73] Assignee: Shiseido Co., Ltd., Tokyo, Japan

[21] Appl. No.: 785,253

[22] Filed: Apr. 6, 1977

[30] Foreign Application Priority Data

Apr. 6, 1976 [JP] Japan .................................. 51-38660

[51] Int. Cl.² .............................................. A61K 7/035
[52] U.S. Cl. ...................................................... 424/69
[58] Field of Search ........................................... 424/69

[56] References Cited

U.S. PATENT DOCUMENTS 3,801,709  4/1974  Augsburger et al. .................. 424/69

*Primary Examiner*—Donald B. Moyer
*Attorney, Agent, or Firm*—Sughrue, Rothwell, Mion, Zinn and Macpeak

[57] ABSTRACT

A cosmetic obtained by treating an inorganic pigment powder with a metal ion blocking agent, drying the product, and mixing a perfume with the resulting pigment. The perfume in the resulting cosmetic is very stable for long periods of time.

16 Claims, 7 Drawing Figures

FIG I

COSMETICS AND PROCESS FOR PREPARATION THEREOF

BACKGROUND OF THE INVENTION

1. Field of the Invention

This invention relates to a cosmetic, particularly to a powdery cosmetic, comprising a blend of a perfume and an inorganic pigment in which the perfume retains its odor for long periods of time, and to a process for preparing the cosmetic.

2. Description of the Prior Art

Some perfumes incorporated in conventional cosmetics containing inorganic pigments emit a fragrant odor just after incorporation, but often change in odor with time. This tendency is remarkable when perfumes are directly incorporated into inorganic pigments, and changes in odor occur over several months or in some cases at the earliest in several days after perfuming. This is because the perfume on the surface of a powder easily contacts the air, and tends to be oxidatively decomposed by the activity (catalytic activity) of the powder itself. Some measures taken in the past against this problem are:

(1) To cause the perfume to be absorbed onto fine particles of silica or a metal soap powder having a relatively low activity, and then add it to a pigment base.

(2) To coat the pigment with a metal soap (for example, as disclosed in Japanese patent publication No. 15394/70).

(3) To avoid the use of perfumes which are susceptible to change.

These measures, however, do not offer a fundamental solution to the problem, but only help to prolong the time until changes occur in the odor of the perfume.

Furthermore, some kinds of perfume still change in odor within very short periods of time, and are therefore useless for cosmetics. For example, a bergamot oil, a perfume of the citrus type, cannot be used for powdery cosmetics, and the manufacturers are forced to neglect the taste for odors of general consumers and to use other more stable perfumes.

Microencapsulated perfumes could be used if the only purpose is to increase the stability with time of perfumes incorporated in inorganic pigments. However, complicated process steps are required to produce perfume-containing microcapsules and the cost of production becomes high. Furthermore, a high level of technique is required, for example, to adjust the wall thickness of the microcapsules so that they will be surely destroyed upon use. Accordingly, the microencapsulation of perfumes has been applied to only very limited special uses.

SUMMARY OF THE INVENTION

It is an object of this invention to provide a cosmetic in which any desired perfume can be used where the perfume odor does not change over long periods of time, and also a process for preparing such a cosmetic.

The above object can be achieved by treating an inorganic pigment powder with a metal ion blocking agent, dehydrating and drying the powder, and blending a perfume with the resulting pigment.

BRIEF DESCRIPTION OF THE DRAWINGS

The drawings are gaschromatographic analyses of the headspace volatiles when talc powder subjected to various treatments was perfumed with 3% bergamot oil.

DETAILED DESCRIPTION OF THE INVENTION

Figure 1:
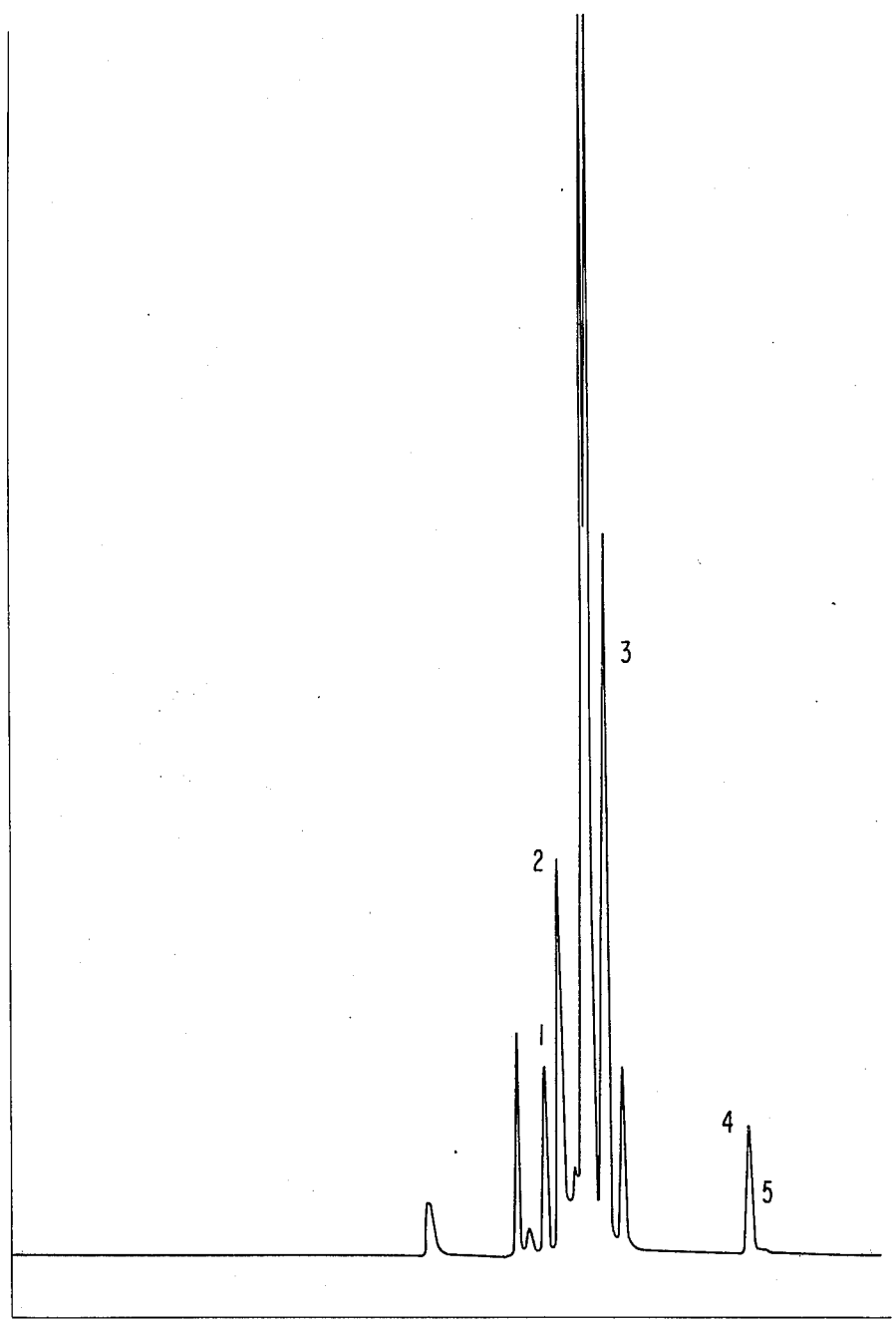
FIG. 1 refers to untreated talc 1 week after perfuming.

The inorganic pigments used in this invention are those heretofore used for cosmetics. In particular, the inorganic pigments used in this invention are those having a specific gravity of about 1 to about 7 and a particle size of about 20 m$\mu$ to about 200$\mu$, which are generally used in cosmetic preparations, but they are not specifically restricted in terms of the particle size of the pigment powder. Specific examples of the inorganic pigments include, for example, oxides and hydroxides of metals (e.g., Mg, Ca, Zn, Al, Ti, Fe, Co, Cr, etc.), such as zinc oxide, titanium dioxide, red iron oxide ($Fe_2O_3$), black iron oxide ($Fe_3O_4$), yellow iron oxide [FeO(OH).n$H_2O$] or alumina; clay minerals such as kaolin (e.g., $Al_2O_3.2SiO_2.2H_2O$), talc ($3MgO.4SiO_2.H_2O$), mica (e.g., $K_2O.2Al_2O_3.6SiO_2.H_2O$) or montmorillonite; metal carbonates such as calcium carbonate or magnesium carbonate, metal sulfates such as barium sulfate or calcium sulfate, silicon compounds such as silica or ultramarine, and ferrocyanide compounds such as Prussian blue. In the present invention, one or a mixture of two or more, of these pigments can be used. A marked odor change inhibiting effect can be obtained when talc is used. Examples of the metal ion blocking agent used in the invention are:

(1) Aminocarboxylic acids of the following general formula, and alkali metal salts thereof.

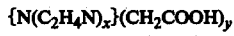

wherein x is 0 or a positive integer and y is a positive integer, with the proviso that $Y = x + 3$ and x is within the range so that, the compound is water-soluble.

Examples of such include nitrilotriacetic acid (NTA) wherein $X=0$ and $y=3$, and Na or K (1, 2 and 3) substitution products at portions H* in the following formula:

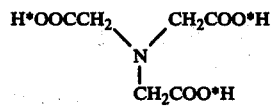

ethylenediaminetetracetic acid (EDTA) wherein $X=1$ and $y=4$, and Na or K (1,2,3, and 4) substitution products at the portions H* in the following formula, or the mono-, di-, tri- and tetratriethanolamine salts thereof:

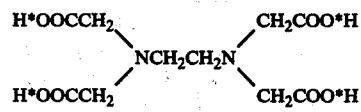

diethylenetriaminopentacetic acid (DPTA) wherein $x=2$ and $y=5$, and its Na or K (1, 2, 3, 4 and 5) substitution products at the portions H* in the following formula:

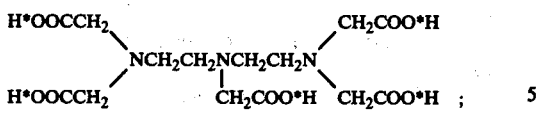

(2) Hydroxyaminocarboxylic acids of the following formula and alkali metal salts thereof:

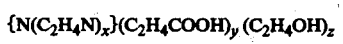

wherein x is 0 or a positive integer, with the proviso that y + z = x + 3, y, z ≧ 1, and x, y and z are within the range so that the compound is water-soluble.

They include, for example, dihydroxyethyl glycine (DEG) wherein x=0, y=1 and z=2 and an Na or K substitution product at the portion H* in the following formula:

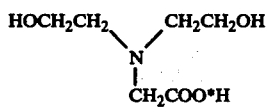

hydroxyethyl ethylenediaminetriacetic acid (HEDTA) wherein x=1, y=3 and z=1, and Na or K substitution products at the portions H* in the following formula:

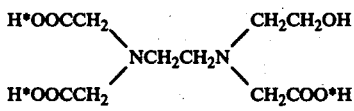

It is to be noted that in the aminocarboxylic acids (1) and in the hydroxyaminocarboxylic acids (2) that, regardless of the value of x, when any one of the —COOH groups in the formula shown is not in the salt form, the solubility in water becomes markedly poor.

(3) Amines of the following general formula:

wherein n is a positive integer within the range so that the compound is water-soluble.

An example thereof is triethylene tetramine (triene), wherein n=3,

or tetraethylene pentamine (tetraene), wherein n=4, and

(4) Organophosphoric acid compounds which are compounds containing 1 to 6 carbon atoms and at least one, preferably 1 to 6 phosphoric acid groups in the molecule and a carbon atom in the matrix nucleus, and their alkali metal salts.

Examples of such include phytic acid (myo inositol hexaphosphoric acid) and Na or K (1, 2 ... 12) substitution products at the portions H* in the following formula:

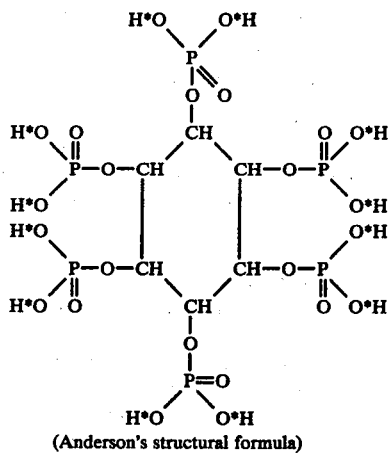

(Anderson's structural formula)

and hydroxyethanediphosphonic acid, and Na or K (1, 2, 3, 4 and 5) substitution products at the portions H* in the following formula:

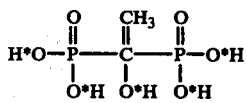

Of the compounds illustrated above, EDTA and its sodium salts give especially good results. A combination of a clay mineral and EDTA (or alkali metal salts thereof) and a combination of an iron oxide and HEDTA (or alkali metal salts thereof) give good results.

The pigment perfumed in accordance with the present invention can be prepared by the following procedure.

First, the inorganic pigment is treated with the metal ion blocking agent to produce a treated pigment. The amount of the blocking agent in the treated pigment is generally about 0.01 to about 10% by weight based on the amount of the untreated pigment powder. If the amount is less than about 0.01% by weight, the effect intended by the present invention is small, and if it is larger than about 10% by weight, the blocking agent precipitates and renders the cosmetic unpleasant to use. A preferred amount is 0.1 to 1% by weight.

Reaction of the blocking agent on the inorganic pigment powder can be accomplished, for example, by immersing the inorganic pigment in an aqueous solution of the blocking agent, or by spraying the aqueous solution onto the pigment powder. The concentration of the blocking agent in the aqueous solution is not particularly limited, but ranges from about 0.0001% by weight to saturation. A preferred concentration range is about 0.01 to about 20% by weight.

The pigment may be merely immersed in the aqueous solution of the blocking agent if desired, but in order to separate the agglomerated particles, it is better to disperse the same therein. When the amount of water is small, the dispersion should be stirred in order to render the reaction system homogeneous. Heating is not particularly required in order to treat the pigment with the blocking agent. The above procedure, however, is generally carried out at a temperature of 0° to 100° C. The time required for treating the pigment with the blocking agent is one which is sufficient to bring the surface of the pigment into contact with the aqueous solution of the blocking agent. Generally, it is about 10 minutes to about 24 hours.

The pigment, after treatment with the blocking agent, may be washed in order to remove any excess blocking agent. Generally, however, this is not necessary. Washing may be performed by repeated dispersion and filtration using deionized water in an amount at least equal to the amount of the pigment.

The pigment treated by the above method may be dried after the treatment when it is used directly as a cosmetic. When the amount of moisture is more than 3% by weight, effects on the product, for example, susceptibility to caking, become greater. Generally, drying should be carried out until the moisture content becomes not more than about 1%.

The drying temperature may be any desired temperature within the range in which sublimation of an antioxidant or the like added to the pigment and coagulation, degeneration or change in odor of the pigment do not occur. When butyl hydroxy toluene or butyl hydroxy anisole is used as an antioxidant, drying is best performed at 40° to 60° C., since these compounds sublime at about 70° C. Pigment not containing such a compound can be dried at higher temperatures. Since the pigment powder generally agglomerates at more than 110° C., drying is usually carried out at about 40° to 110° C., preferably 90° to 100° C. When a spray drying which can prevent agglomeration, is employed, higher drying temperatures at which degeneration or changes in odor do not occur, generally temperatures of not more than about 300° C., can be chosen.

The pigment obtained in the above manner can be directly perfumed to use it as a cosmetic. In general, the perfume can be present in an amount of about 0.1 to about 5% by weight based on the pigment weight.

The stability of the perfume incorporated in the pigment can be further increased by treating the pigment powder with a metallic soap before or after treatment with the blocking agent in accordance with the present invention. The metallic soap generally denotes an Al, Mg, Ca, Zn, Ba or Li salt of a straight-chain fatty acid containing 10 to 22 carbon atoms.

The metallic soap treatment can be accomplished by treating the pigment powder with an aqueous solution of a metal salt and an aqueous solution of a fatty acid soap separately before or after the treatment with the blocking agent. The pigment powder is treated first with either one of the two aqueous solutions and then with the other. For example, the pigment powder can be dispersed in an aqueous solution of a metal salt, and the dispersion stirred to obtain the pigment treated with the metal salt. Then, the pigment is dried (e.g., as described hereinbefore), pulverized (if necessary), and added to an aqueous solution of the fatty acid soap. The mixture is stirred to form a metallic soap in lumps on the surface of the pigment. The product is then dehydrated and dried, and the resulting powder recovered. (The above method is described, for example, in Japanese patent publication No. 15394/70).

When the treatment with the aqueous solutions of fatty soap is first carried out, the same procedure can be employed.

The metal salt used includes, for example, water-soluble salts of aluminum, magnesium, calcium, zinc, barium and lithium, such as the hydrochlorides, sulfates, nitrates or hydroxides. The fatty acid soaps that can be used are generally sodium or potassium salts of straight-chain saturated fatty acids containing 10 to 22 carbon atoms.

The concentration of the aqueous solution of metal salt, which differs according to the type of the metal salt, is generally 1 to 20% by weight, and at a desired temperature, i.e., generally 20° to 95° C., the pigment is contacted with the aqueous solution of metal salt for about 10 to about 60 minutes.

The concentration of the aqueous solution of fatty acid soap is generally 1 to 20% by weight, and at a desired temperature, i.e., generally 60° to 90° C., the pigment is contacted with the aqueous solution of fatty acid soap for about 10 to about 60 minutes.

The amount of the metallic soap most effective to treat the pigment is generally about 0.1 to about 20% by weight, based on the untreated pigment, preferably 0.3 to 7% by weight. When the amount is increased beyond 20% by weight, the effect scarcely changes, but the metallic soap is difficult to adhere to the pigment.

When the pigment is treated with the above two solutions, stirring is preferably performed. After the treatment, the treated product is washed with water, e.g., about 10 times, until the unreacted substances and by-products no longer dissolve in water. The effect obtained by the blocking agent is reduced if this washing operation is insufficient. When the pigment after treatment with a metallic soap is directly used as a cosmetic, it is preferably dried until the moisture content thereof becomes not more than about 3% by weight, especially not more than 1% by weight. Drying is carried out at a temperature of not more than the decomposition temperature of the metallic soap (generally 250° to 300° C), generally at 90° to 100° C. When the treatment with the blocking agent is carried out after treatment with the metallic soap, only the washing may be carried out without performing the drying step.

When the pigment which has already been treated with the metal ion blocking agent is contacted with the aqueous solutions for treatment with metal soap, the blocking agent on the surface of the pigment sometimes dissolves in water. In such a case, the treatment may be carried out by adding the pigment to a solution of metallic soap in a low-boiling organic solvent such as benzene, toluene or xylene, and then the solvent removed.

When the treatment with metallic soap is carried out before or after the treatment with the blocking agent, the method of treatment with the blocking agent and the amount of the blocking agent in the pigment are the same as those earlier described above with regard to pigment not contacted with the metallic soap.

When the pigment is subjected to these two treatments, the effect of preventing the change of the odor of the perfume incorporated is far greater than in the case of performing either one of the metallic soap treatment or the metal ion blocking treatment alone.

When an antioxidant is added to the pigment in accordance with the present invention, the effect of preventing the change of the odor of the perfume in the pigment powder can be further enhanced. The type and amount of the antioxidant may be the same as those heretofore used in cosmetics. For example, butyl hydroxy toluene (BHT), butyl hydroxy anisole (BHA), vitamin E, and Antracine 20, 22 (trademarks, Naarden, Holland) are commonly used. Of these BHT gives the best results. The amount of the antioxidant is generally about 0.0001 to about 0.2% by weight based on the untreated pigment.

The antioxidant may be added at any stage in the process of preparing the pigment in accordance with the present invention. For example, the antioxidant may be added to an aqueous solution during the preparation of the pigment in accordance with the present invention. When the pigment is to be treated with metallic soap, the antioxidant may be used dissolved in the fatty acid. Or the antioxidant may be used dissolved in an organic solvent, e.g., ethyl alcohol. The solvent is evaporated off from the pigment.

Other additives that can be used in this invention are those as heretofore added to cosmetics, such as ultraviolet absorbents, antiseptics, germicides, etc.

In order to prevent the blocking agent adhering to the pigment surface from being removed together with the aqueous solution when recovering the pigment powder from the aqueous solution after treatment, a small amount, that is, 0.1 to 3% by weight based on the amount of the untreated pigment, of a tacky substance such as carboxymethyl cellulose, hydroxyethyl cellulose or polyvinyl alcohol may be added to the treating solution to be finally used. This method is useful when drying the pigment by spray drying.

Conventional methods can be directly employed to perfume the pigment powder treated and dried in accordance with the present invention. When the pigment in accordance with this invention is to be used for fragrant powders, solid powders or oily powders, an oil for improving the usability of powder (to give a moist feeling), such as deodorized squalene, a surface active agent such as sorbitan monopalmitate or isopropyl myristate, a flowable oil such as liquid paraffin or isopropyl myristate, and a solidifying agent as carnauba wax, solid paraffin or deodorized lanolin may be mixed with the pigment in accordance with conventional practices. A perfume may be added before, during or after the mixing of the pigment with these additives.

As will be described hereinbelow with reference to the Examples, the pigment used in the present invention offers the marked advantage that it not only increases the stability of perfumes used heretofore in powdery cosmetics, but also makes it possible to use those perfumes which heretofore could not be used for perfuming powdery cosmetics, for example, citrus type perfumes (e.g., bergamot oil), perfumes containing relatively high amounts of an ester group (especially, an acetate or formate group) such as lavender oil and lavandin oil and perfumes containing terpene compounds (which are also included within the first-mentioned two types of perfumes).

The mechanism of this noteworthy advantage of the invention has not yet been made fully clear, but it is believed that the catalytic activity of the powdery pigment can be markedly reduced by: (1) the chelation of metal ions which are on the surface of the powdery pigment or have dissolved out; and (2) the chemical bonding or physical absorption of the blocking agent onto active sites on the pigment surface which show a solid acid or solid base.

The perfume stabilizing effect of the pigment used in this invention is described below.

Various specimens obtained by blending 3% bergamot oil with pigments produced by various combinations of treatment with a metal ion blocking agent 7, treatment with a metallic soap [4, 5, 6], and treatment with an antioxidant 3, and allowing the products to stand in a closed system for 1 month at 37° C. were evaluated for odor by a panel of five specialists. Furthermore, the headspace volatiles (volatile components at 25° C.) of these specimens were analyzed by gas chromatography.

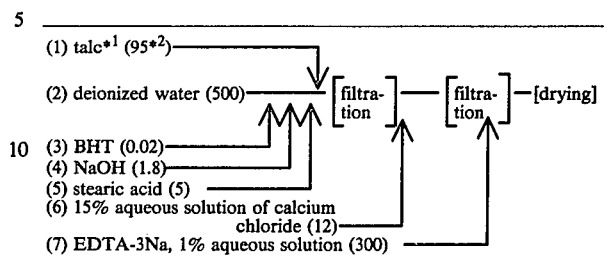

(1) talc*[1] (95*[2])
(2) deionized water (500)
(3) BHT (0.02)
(4) NaOH (1.8)
(5) stearic acid (5)
(6) 15% aqueous solution of calcium chloride (12)
(7) EDTA-3Na, 1% aqueous solution (300)

Figure 2:
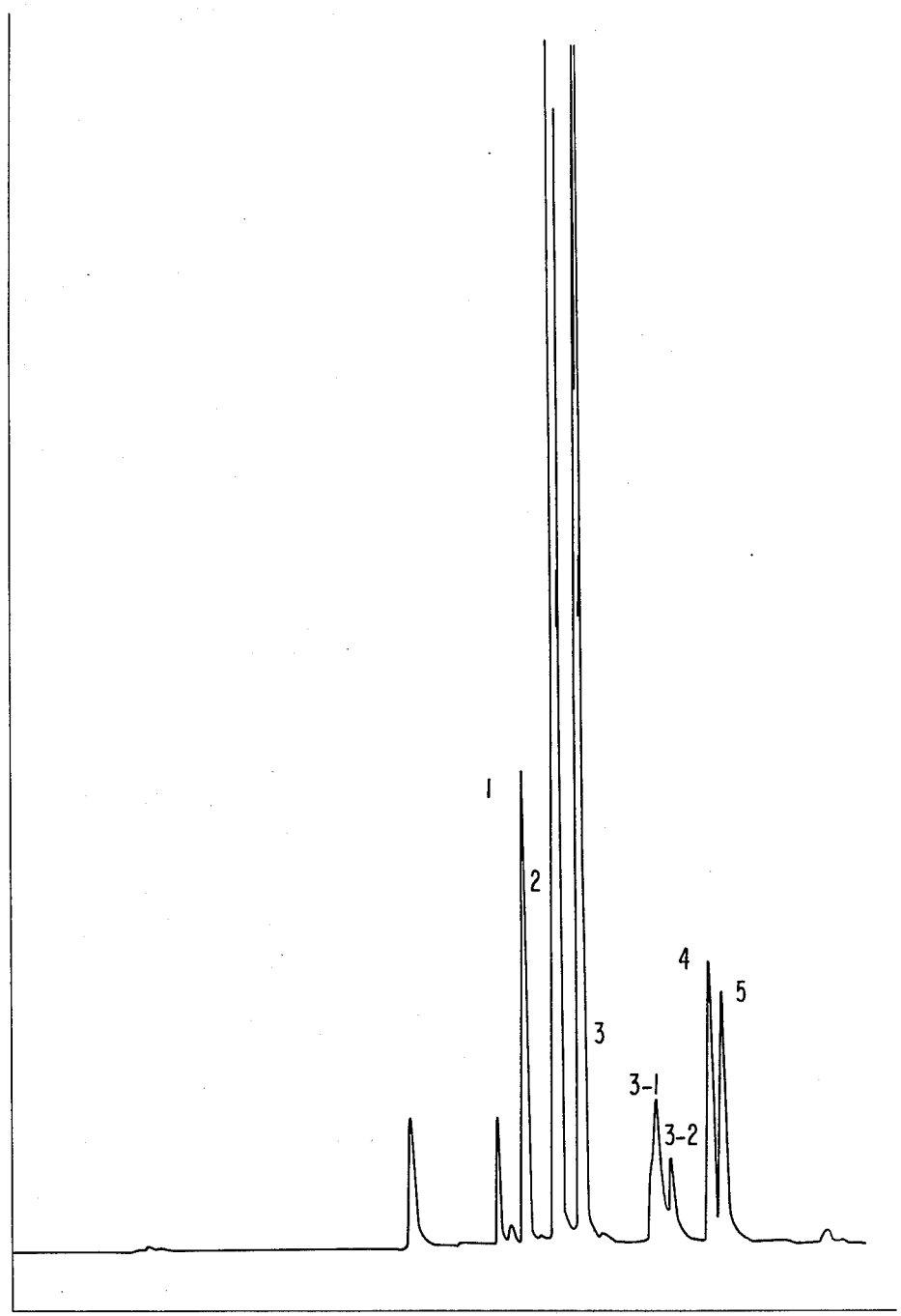
FIGS. 2 to 6 refer to talc subjected to various treatments 1 month after perfuming.
Figure 3:
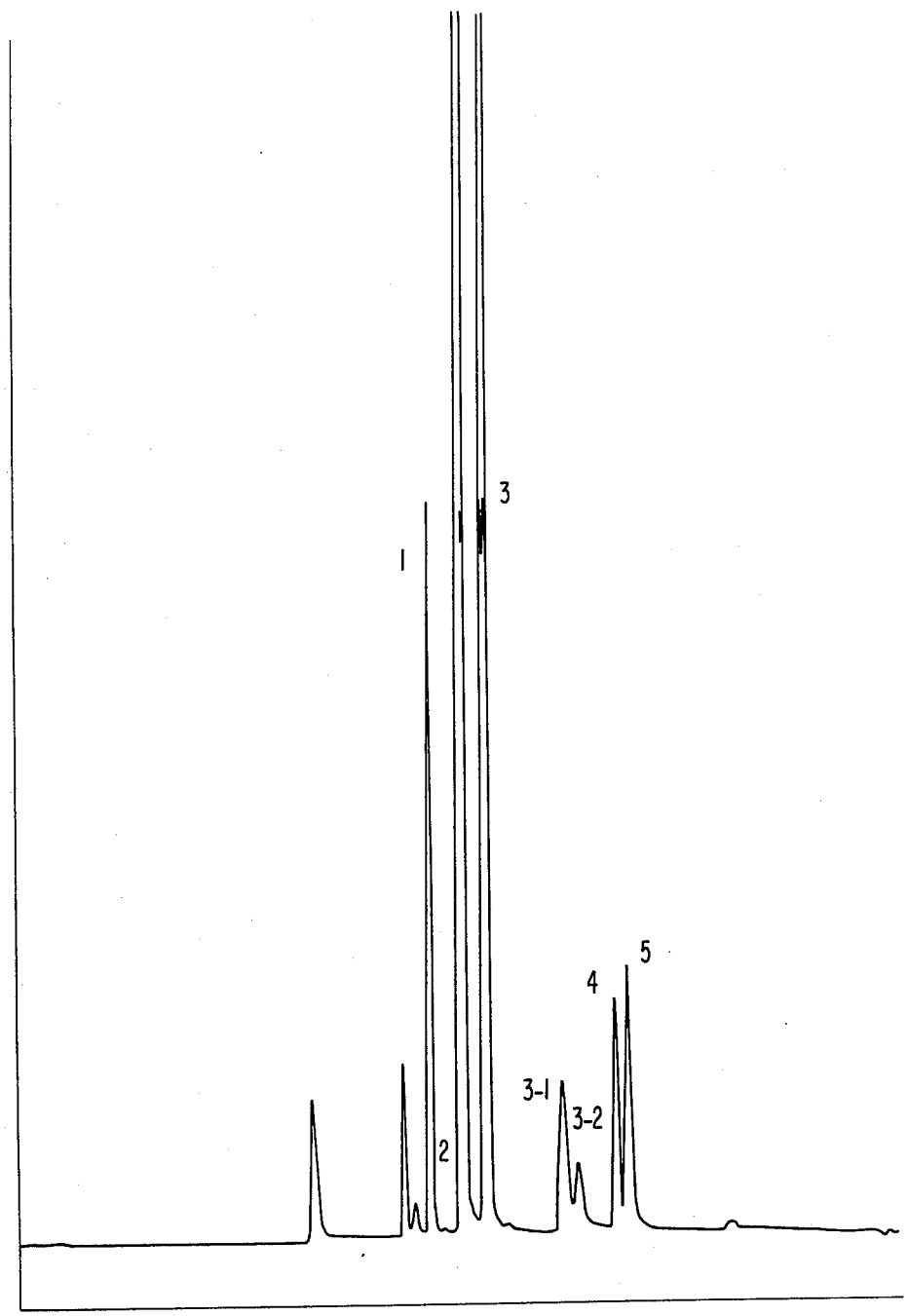
Figure 4:
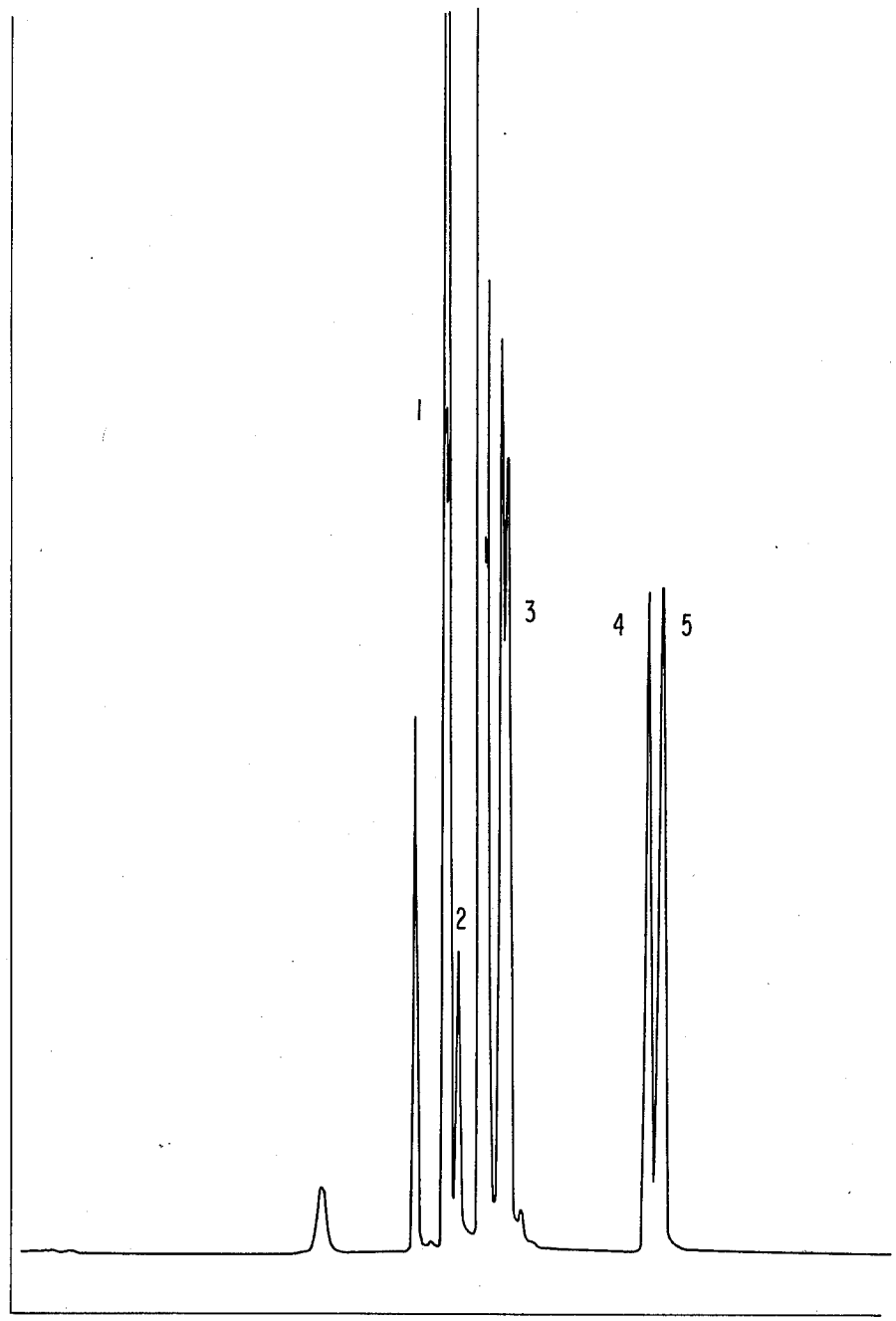
Figure 5:
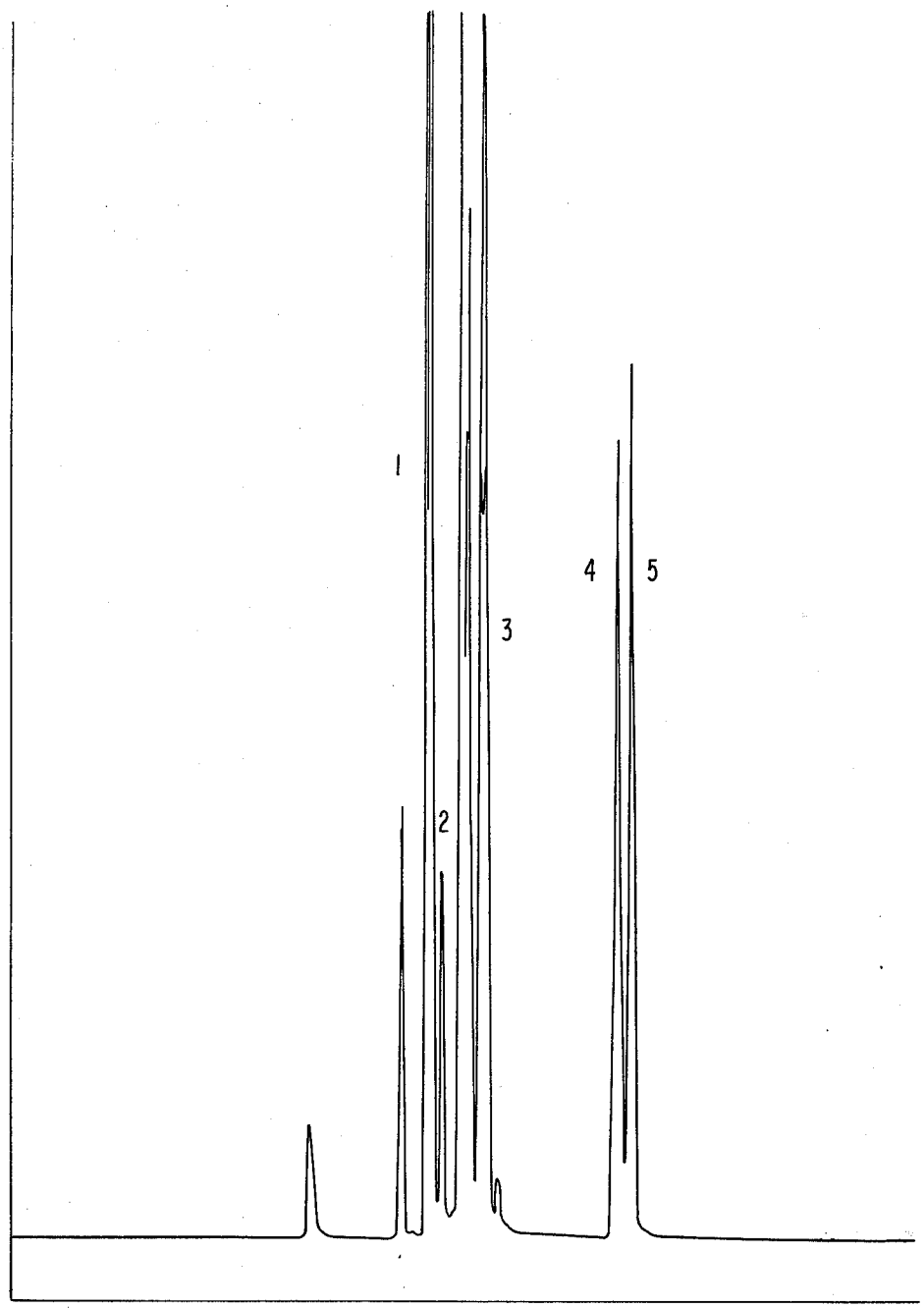
Figure 6:
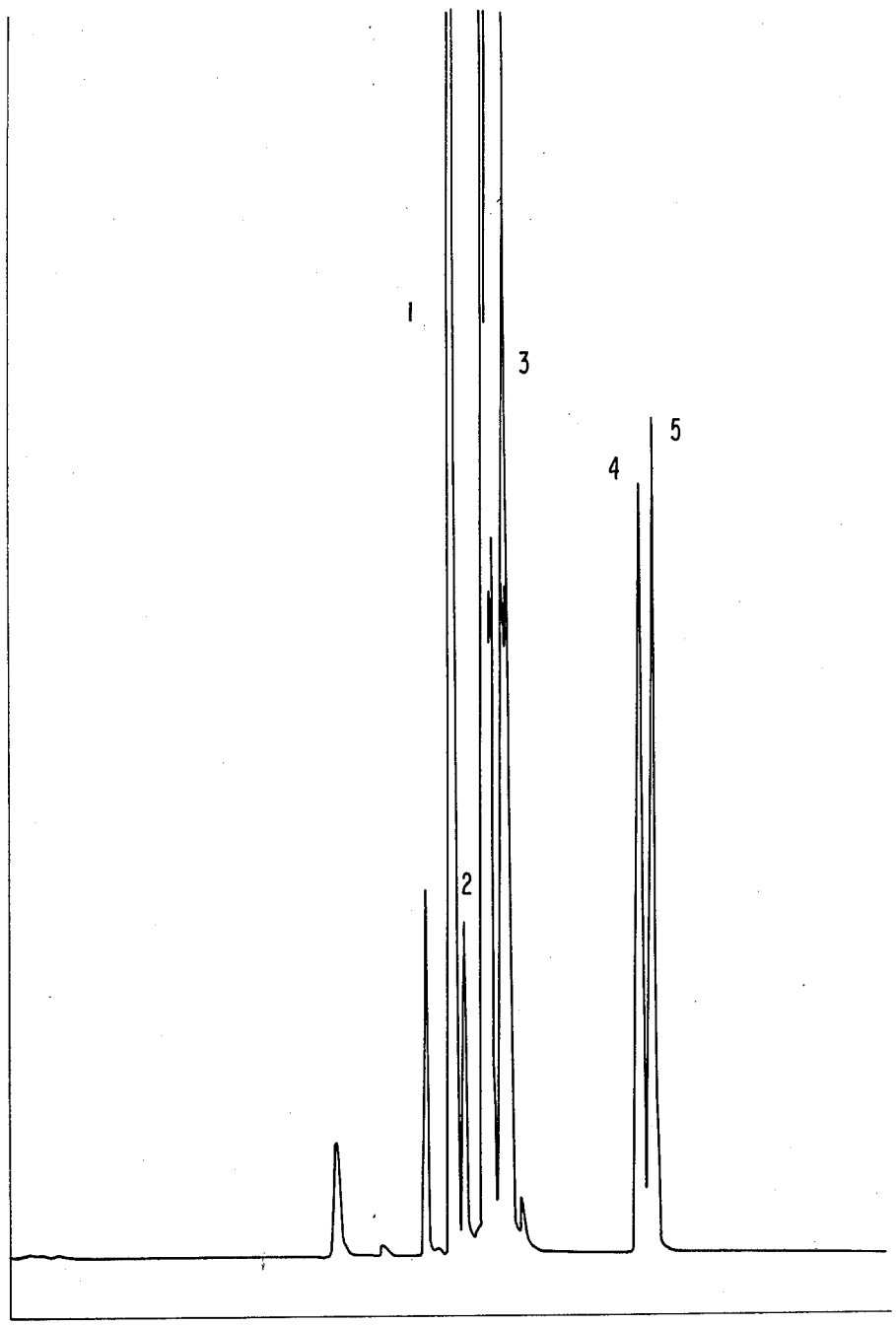

*[1] Specific gravity:
Particle size distribution: 2 to 14 μ
Specific volume on tapping: 1.56 cc/g
(The specific volume on tapping denotes the apparent volume of the pigment per g after the pigment in a graduated test tube was tapped by permitting the test tube to fall 400 times from a height of 10 cm).
*[2] The figures in the parentheses are parts by weight.
The results of the above tests were as follows:

| Speci- | Treatments | | | Evaluation | Gas |
| men | (3) | (4), (5), (6) | (7) | of odor | chromatogram |
|---|---|---|---|---|---|
| 1* | No | No | No | Poor | Figure 1 |
| 2 | No | Yes | No | Fair | Figure 2 |
| 3 | Yes | No | No | Fair | — |
| 4 | Yes | Yes | No | Good | Figure 3 |
| 5 | No | No | Yes | Excellent | Figure 4 |
| 6 | No | Yes | Yes | Excellent | Figure 5 |
| 7 | Yes | No | Yes | Excellent | — |
| 8 | Yes | Yes | Yes | Excellent | Figure 6 |

*On standing at 37° C for one week.
The standards of evaluation were as follows:
Excellent: No difference was seen from the specimen immediately after perfuming.
Good: Some difference was seen from the specimen immediately after perfuming.
Fair: A considerable difference was seen from the specimen immediately after perfuming.
Poor: Quite different from the specimen immediately after perfuming As can be seen from the Table, a product obtained by perfuming an untreated pigment (Specimen No. 1) emitted an odor quite different from immediately after perfuming upon standing for 1 week at 37° C. But when using pigments produced by immersion in a metal ion blocking agent (EDTA-3Na), followed by filtration and drying, the odor did not change even after standing for 1 month at 37° C. (the conditions being very severe for perfumes). The metallic soap treatment and the antioxidant treatment, when performed either alone or in combination contributed somewhat to stabilize the perfume, but the degree of stabilization was far lower than in the case of treatment with a metal ion blocking agent alone.

Figure 7:
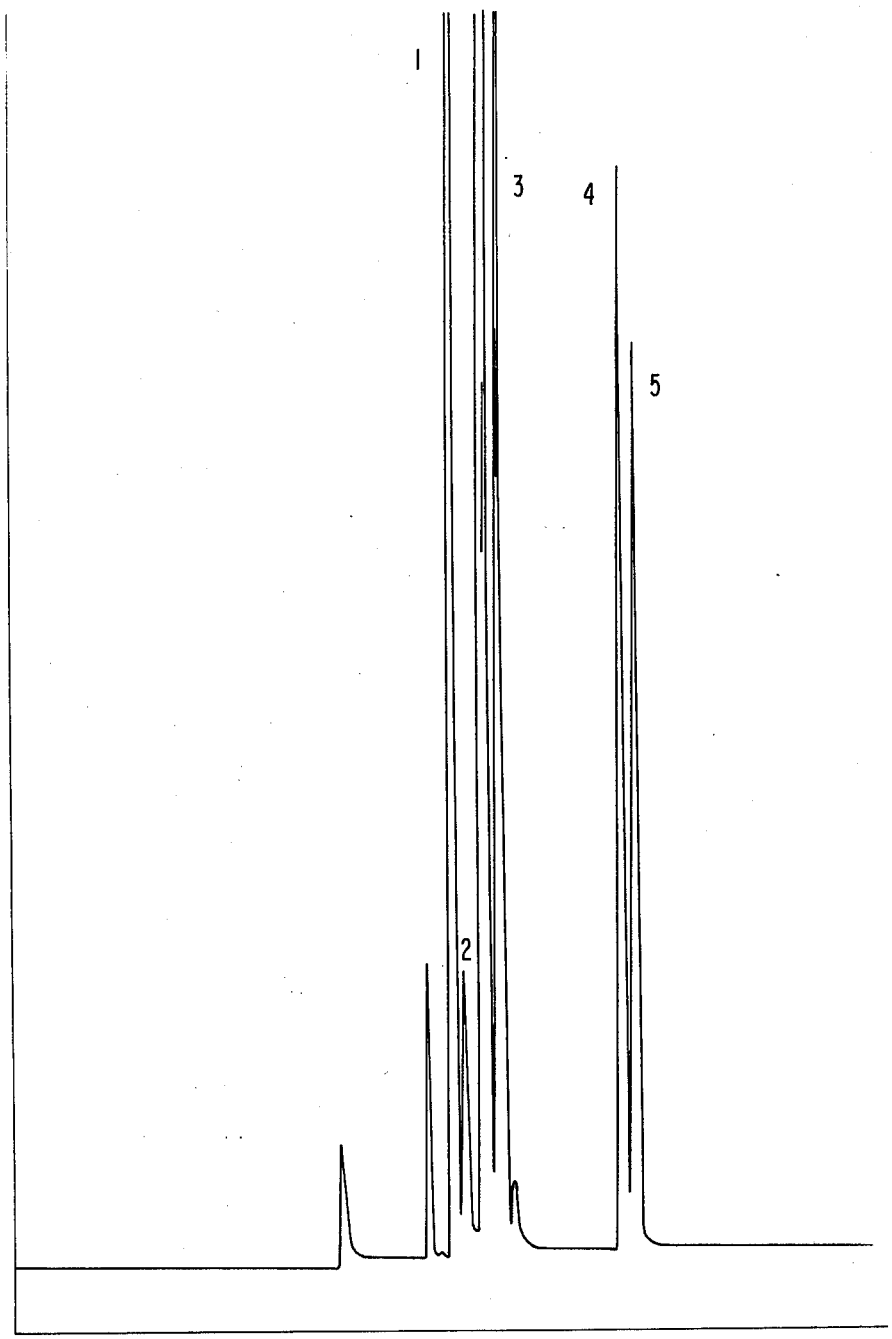
FIG. 7 refers to talc treated with a metal soap, immediately after perfuming.

The gaschromatographic analyses of the headspace volatiles of the specimens are shown in FIGS. 1 to 6. FIG. 7 is a gaschromatographic analysis of the headspace volatile of specimen No. 2 immediately after it was perfumed with 3% bergamot oil. The effect of the present invention is clear from a comparison of FIGS. 1 to 6 with FIG. 7. In FIGS. 1 to 3 (not treated in EDTA-3Na), the peaks at 1, 2, 4 and 5 decrease, and particularly in FIGS. 2 and 3, peaks 3-1 and 3-2 appear. However, in FIGS. 4 to 6 (treated in EDTA-3Na), these peaks scarcely change.

The safety of the talc powder in specimen No. 8 was determined by a primary skin irritation test on rabbits, an eyelid irritation test, an acute oral toxicity test on mice, and a closed human patch test on 47 healthy women. As a result, no difference was seen from untreated talc powder conventionally used in cosmetics; it was thus confirmed that the treated pigment used in this invention have a very high degree of safety.

In the present invention, the effect is almost the same when the order of the metal ion blocking treatment and the metallic soap treatment is reversed.

The following Examples illustrate the production or use of pigments used in this invention. In all of these examples, where no temperature is specifically mentioned, it means that the treatment were carried out at room temperature (15° to 25° C.). Furthermore, unless otherwise indicated, all parts and percentages in these examples are by weight, and all processings in these examples were carried out at atmospheric pressure.

EXAMPLE 1

100 parts of rutile type titanium oxide (specific gravity 4.2 g/cc; particle size distribution 0.2 to 1.2 μ) was dispersed at 80° C. for 3 hours in 150 parts of an aqueous solution containing 0.1% of heptasodium phytate and 0.1% of sodium carboxymethyl cellulose (average degree of polymerization about 300; degree of etherification 0.66; viscosity (2% aq. solution at 25° C.) 100 cps) thus treated titanium oxide was dried by a spray dryer (an atomizer made by Niro Company: air blasting temperature 250° C.; air discharging temperature 120° C.; the rotating speed of the atomizer 30,000 rpm) to form 90 parts of a pigment to be perfumed.

EXAMPLE 2

In a reaction kettle equipped with a stirrer, 0.8 part of sodium hydroxide was dissolved in 500 parts of deionized water, and 95 parts of a red iron oxide pigment ($\alpha$-$Fe_2O_3$, specific gravity 4.5 g/cc, size distribution 0.08 to 0.8 μ) was dispersed in the solution. In a separately prepared heating kettle, 4.5 parts of myristic acid was melted at 70° C., and 0.01 part of dibutylhydroxy toluene was dissolved therein. The solution was added to the dispersion mentioned above, and the mixture stirred for 30 minutes to perform a saponification reaction. Then, while maintaining the temperature at 70° to 80° C., 12 parts of a 15% aqueous solution of calcium chloride was added dropwise. After the addition, the mixture was stirred for another 60 minutes to form a metallic soap by double decomposition. The metallic soap was filtered, washed with water, and then dispersed in 200 parts of a 0.5% aqueous solution of trisodium hydroxyethyl ethylenediaminetriacetate uniformly for 6 hours. The dispersion was filtered, and then dried for 72 hours in a hot air dryer (45° to 55° C.) to form 98 parts of a pigment to be perfumed.

EXAMPLE 3

90 parts of talc (particle diameter 2 to 20 μ; specific gravity 2.7 g/cc) was uniformly dispersed for 24 hours in a 0.1% aqueous solution of EDTA-3Na, filtered, and then dried at 90° C. for 8 hours by a hot air dryer. The dried product was dispersed in 200 parts of benzene in which 5% of zinc stearate and 0.001% of butylhydroxy anisole were dissolved. After 1 hour, the dispersion was dried at 40° to 45° C. and 10 mmHg for 5 hours in a vacuum dryer equipped with a device to recover solvent, to thereby form 95 parts of a pigment to be perfumed.

EXAMPLE 4

| Fragrant powder | | |
|---|---|---|
| Recipe | | |
| (1) Pigment obtained in Example 3 | 97.0 parts | |
| (2) Deodorized squalene | 1.5 | |
| (3) Blended perfume * | 1.5 | |
| | Total | 100.0 parts |

(1) above was charged into a ribbon blender, and, with stirring, (2) above was uniformly sprayed therein with a spray gun. Subsequently, (3) above was sprayed thereon in the same manner to perfume the pigment. After perfuming, the mixture was stirred for another 60 minutes, and passed through a 150-micron sieve to form a fragrant powder.

A sample of fragrant powder immediately after production and a sample which was left to stand for one month at 37° C. were tested for odor by a panel of five specialists and the headspace volatiles were analyzed by gas chromatography. In both of these tests, no difference was observed between the two specimens.

The blended perfume (*) shown in the above recipe was prepared in accordance with the following recipe.

| | | |
|---|---|---|
| Bergamot Oil | 360 | parts |
| Lemon Oil | 110 | |
| Orange Oil | 50 | |
| Lavender Oil | 120 | |
| Neroli Oil | 60 | |
| Geranium Oil | 50 | |
| Musk Ketone | 40 | |
| Musk Ambrette | 80 | |
| Coumarin | 40 | |
| Absolute Oakmoss | 20 | |
| Sandal Wood Oil | 20 | |
| Methyl Dihydro Jasmonate | 50 | |
| | Total 1000 | parts |

EXAMPLE 5

| Pressed powder | | |
|---|---|---|
| Recipe | | |
| (1) Pigment obtained in Example 3 | 93.0 parts | |
| (2) Pigment obtained in Example 2 | 0.4 | |
| (3) Pigment obtained as in Example 2 except using yellow iron oxide (particle size 0.08 to 0.8μ; specific gravity 4.1 g/cc) instead of the red iron oxide | 0.6 | |
| (4) Deodorized lanolin | 2.0 | |
| (5) Mineral oil (Hiwhite #120, produced by Nippon Oil Co., Ltd.; viscosity (25° C) 35.82 cps; specific gravity 0.856) | 2.0 | |
| (6) Sorbitan monopalmitate | 1.0 | |
| (7) Blended perfume * | 1.0 | |
| | Total | 100.0 parts |

(1), (2) and (3) above were mixed in a planetary mixer equipped with a spray device. A mixture of (4), (5) and (6) above, which had been previously melt-mixed in a heating kettle at 60° C. for 30 minutes, and (7) above were successively sprayed while mixing was continued. The mixing was then continued for another 1 hour. The mixture was then pulverized by a hammer mill having a 2 mm screen. The pulverized product was passed through a 150-micron sieve, and molded into a circular plate by a hydraulic automatic molding machine at 16 pounds/inch², to form a solid powder whose odor did not change for extended periods of time.

The solid powder obtained was tested in the same way as in Example 4, and it was found that no change in odor was observed even after standing for 1 month at 37° C.

The blended perfume (*) shown in the above recipe was prepared in accordance with the following recipe.

| Bergamot Oil | 300 parts |
|---|---|
| Sweet Orange Oil | 170 |
| Clove Oil | 40 |
| Angelica Seed Oil 10% | 30 |
| Absolute Rose | 30 |
| Absolute Oakmoss | 70 |
| Patchouli Oil | 50 |
| Vetiver Oil | 30 |
| Absolute Jasmin | 50 |
| Musk Ketone | 40 |
| Musk Ambrette | 40 |
| Benzoin | 60 |
| Absolute Cist-Labdanum | 10 |
| Aldehyde C-14 10% | 10 |
| Methyl Ionone | 20 |
| Galaxolide 50 | 50 |
| Total | 1000 parts |

EXAMPLE 6

| Recipe | Foundation |
|---|---|
| (1) Pigment obtained in Example 1 | 20.0 parts |
| (2) Pigment obtained as in Example 1 using kaolin instead of the titanium oxide | 20.0 |
| (3) Pigment obtained as in Example 1 using red iron oxide instead of the titanium oxide | 0.9 |
| (4) Pigment obtained as in Example 1 using yellow iron oxide instead of the titanium oxide | 2.0 |
| (5) Pigment obtained in the same way as in Example 1 using black iron oxide instead of the titanium oxide | 0.1 |
| (6) Mineral Oil (Hiwhite #120, produced by Nippon Oil Co., Ltd.; viscosity (25° C) 35.82 cps; specific gravity 0.856) | 40.0 |
| (7) Sorbitan sesquioleate | 1.5 |
| (8) Isopropyl myristate | 7.5 |
| (9) Carnauba wax (produced by Noda Wax Co., Ltd.; specific gravity 0.99; melting point 83-85° C) | 2.0 |
| (10) Paraffin wax (Aristowax 145° F, produced by Union Oil Co,; specific gravity 0.90; melting point 63° C) | 5.0 parts |
| (11) Blended perfume * | 1.0 |
| Total | 100.0 parts |

The particle diameters and specific gravities of the pigments used were as follows:

| Pigment | Particle diameter (μ) | Specific gravity (g/cc) |
|---|---|---|
| Kaolin | 0.2 to 5 | 2.8 |
| Red iron oxide | 0.08 to 0.8 | 4.5 |
| Yellow iron oxide | 0.08 to 0.8 | 4.1 |
| Black iron oxide | 0.2 to 0.6 | 5.0 |

In a mixer equipped with a stirring vane and a homomixer, (6) to (10) above were melt-mixed for 60 minutes at 80° to 85° C. A mixture of (1) to (5) above obtained by mixing in a high-speed rotating mixer for 5 minutes at 1800 rpm was added to the melt-mix while continuing mixing. At the end of the addition, the mixture was dispersed for 30 minutes at 200 rpm using the homomixer while maintaining the temperature at 80° to 85° C. Evacuation was performed at 5 mmHg for 40 minutes, and (11) above was then added. The mixture was stirred for 15 minutes at low speed. The mixture was loaded into a receptacle from a metering loader at 80° to 85° C., and cooled in cold air at 20° C. to afford an oily powder which did not change in odor over extended periods of time.

The oily powder was tested in the same way as in Example 4, and it was found that no change in odor was observed even on standing for 1 month at 37° C.

The blended perfume (*) given in the above recipe was prepared in accordance with the following recipe.

| Citrus type blended perfume | 35.5 parts |
|---|---|
| Carnation-type blended perfume | 20 |
| Jasmine-type blended perfume | 24.5 |
| Musk-type blended perfume | 20 |
| Total | 100.0 parts |

While the invention has been described in detail and with reference to specific embodiments thereof, it will be apparent to one skilled in the art that various changes and modifications can be made therein without departing from the spirit and scope thereof.

What is claimed is:

1. A process for preparing a cosmetic powder which comprises treating an inorganic pigment powder with a metal ion blocking agent, dehydrating and drying the treated powder, treating the inorganic pigment powder with a metallic soap before or after treatment with the metal ion blocking agent, and blending the resulting pigment with a perfume.

2. The process of claim 1 wherein said inorganic pigment is at least one member selected from the group consisting of oxides and hydroxides of metals, clay minerals, metal carbonates, metal sulfates, silicon compounds and ferrocyanide compounds.

3. The process of claim 1 wherein said inorganic pigment is at least one member selected from the group consisting of zinc oxide, titanium oxide, red iron oxide, black iron oxide, yellow iron oxide, alumina, kaolin, talc, mica, montmorillonite, calcium carbonate, magnesium carbonate, barium sulfate, calcium sulfate, silica, ultramarine and Prussian blue.

4. The process of claim 1 wherein said metal ion blocking agent is at least one member selected from compounds of the following formulae (1), (2) and (3), and organophosphoric compounds:

$$\{N(C_2H_4N)_x\} (CH_2COOH)_y \quad (1)$$

wherein x is 0 or a positive integer, and y is a positive integer, with the proviso that y = x + 3;

$$\{N(C_2H_4N)_x\} (CH_2COOH)_y(C_2H_4OH)_z \quad (2)$$

wherein x is 0 or a positive integer, y + z = x + 3, and y, z ≧ 1; and $$N(NHC_2H_4)_n NH_2 \quad (3)$$

wherein n is a positive integer.

5. The process of claim 1 wherein said metal ion blocking agent is selected from the group consisting of nitrolotriacetic acid, ethylenediaminetetracetic acid, diethylenetriaminopentacetic acid, and alkali metal salts of these acids; dihydroxyethyl glycine, hydroxyethylethylenediaminetriacetic acid, and alkali metal salts of these acids; triethylene tetramine, and tetraethylene pentamine; and phytic acid, hydroxyethane diphosphonic acid and alkali metal salts of these acids.

6. The process of claim 1 wherein the amount of the metal ion blocking agent in the treated pigment is about 0.01 to about 10% by weight based on the amount of the untreated pigment powder.

7. The process of claim 1 wherein the treatment with the metal ion blocking agent is carried out by dipping the pigment powder in an aqueous solution of the metal ion blocking agent.

8. The process of claim 1 wherein an antioxidant is added in any desired step in the process of preparing the cosmetic.

9. The cosmetic of claim 1 wherein the cosmetic is a fragrant powder, solid powder or oily powder.

10. A cosmetic comprising an inorganic pigment powder treated with both a metal ion blocking agent and a metallic soap, and a perfume blended therewith.

11. The process of claim 10 wherein the metallic soap is an Al, Mg, Ca, Zn, Ba or Li salt of a straight chain saturated fatty acid containing 10 to 22 carbon atoms.

12. The process of claim 10 wherein the amount of the metallic soap in the pigment treated with the metallic soap is about 0.1 to about 20% by weight based on the amount of the untreated pigment.

13. The process of claim 10 wherein the treatment with the metallic soap is carried out by first treating the pigment treated or untreated with the metal ion blocking agent, with one of an aqueous solution of an alkali metal salt of a fatty acid and an aqueous solution of a metal salt, and then treating the product with the other.

14. The process of claim 10 wherein the metallic soap treatment is carried out by dipping the pigment treated or untreated with the metal ion blocking agent in an organic solvent solution of the metallic soap.

15. The cosmetic of claim 10 wherein the inorganic pigment powder to be treated with the metal ion blocking agent is pre-treated with a metallic soap.

16. The cosmetic of claim 10 wherein the inorganic pigment treated with the metal ion blocking agent is further treated with a metallic soap.

* * * * *